United States Patent [19]

Stultz

[11] 4,246,775
[45] Jan. 27, 1981

[54] POROSITY MEASURING APPARATUS AND PERFORATING SYSTEM USING SAME

[75] Inventor: Edward B. Stultz, Richmond, Va.

[73] Assignee: Philip Morris Incorporated, New York, N.Y.

[21] Appl. No.: 46,966

[22] Filed: Jun. 8, 1979

[51] Int. Cl.³ .......................................... G01N 15/08
[52] U.S. Cl. ...................................... 73/38; 73/159; 219/384
[58] Field of Search ............... 219/383, 384; 73/38, 73/159; 166/12, 228; 131/21R

[56] References Cited

U.S. PATENT DOCUMENTS

| 3,056,281 | 10/1962 | Smyth | 73/38 |
| 3,466,925 | 9/1969 | Ziegenhagen et al. | 73/38 |
| 4,118,619 | 10/1978 | McArthur et al. | 219/384 X |
| 4,121,595 | 10/1978 | Heitmann et al. | 131/21 R |

FOREIGN PATENT DOCUMENTS 980058 1/1965 United Kingdom.

OTHER PUBLICATIONS

Edenborough, L. D., How Wiggins... Porosity Meter, Sep. 12, 1966, from Paper Trade Journal - England, pp. 62-66.

Primary Examiner—Jerry W. Myracle
Attorney, Agent, or Firm—Watson, Leavenworth, Kelton & Taggart

[57] ABSTRACT

Porosity measuring apparatus for a moving web of sheet material comprising a sensor having a chamber and a wall provided with apertures communicating with the chamber and of number, spacing and dimension sufficient to obtain an air seal between the moving web and wall during application of a vacuum to the chamber.

24 Claims, 11 Drawing Figures

POROSITY MEASURING APPARATUS AND PERFORATING SYSTEM USING SAME

BACKGROUND OF THE INVENTION

This invention pertains to porosity measuring and, in particular, to a porosity measuring apparatus for providing porosity control for perforating systems.

Perforating systems have been widely used for perforating a variety of sheet materials. One such sheet material is paper used in the construction of cigarettes. In perforating cigarette paper and, in particular, cigarette tipping paper, it is essential that the porosity of the resultant perforated paper be strictly controlled. In this manner, porosity variation and, correspondingly, variation in dilution of resultant cigarettes can be held within desired limits.

The porosity of a web of sheet material undergoing perforation can vary due to variations in web characteristics as well as variations in operating characteristics of the particular perforating system being used. A number of techniques have been devised for monitoring web porosity and for using the monitored porosity to control system operation to obtain a desired porosity. U.S. Pat. No. 4,025,752 describes one such technique wherein the porosity of a moving web perforated by electric sparks is monitored. A vacuum is applied to a chamber provided with an opening in facing relationship to the web. Variations in web porosity result in changes in the vacuum established within the chamber. These changes in vacuum cause corresponding changes in pressure which are monitored by a pressure detector.

The output electrical signal of the pressure detector is compared with a preselected or preset electrical signal representative of desired web porosity. The resultant difference signal is further processed by amplification and by multiplication with a signal representative of web speed. Circuitry for controlling the pulse generator at the electric spark perforating station is responsive to the processed signal and provides electric discharges which result in a web porosity which tracks desired web porosity in typical control system fashion.

U.S. Pat. No. 4,121,595 discloses another technique wherein web porosity is measured indirectly and utilized to control system components to ensure desired porosity. In this case, a moving web of tipping paper is perforated in a row pattern by a perforating assembly comprising a laser beam and cooperating optics. The perforated paper is then applied to the filter plug region of cigarette rods of double unit length which are subsequently severed to form individual cigarettes. The individual cigarettes are conveyed to a testing station whereat the average permeability or porosity of the cigarettes is measured and the measured porosity compared to a desired range of porosity values. Deviation from this desired range results in a signal which is used to vary the characteristics of the perforating laser beam so as to provide perforations which cause the porosity of the resultant cigarettes to lie within the desired porosity range.

In this system, the testing station comprises a testing chamber at which testing fluid from a constant pressure source is passed through the cigarette under test. A transducer having a diaphragm is responsive to the pressure of the fluid as it leaves the cigarette and this diaphragm controls a capacitor which supplies signals to an integrating circuit. The output of the integrating circuit corresponds to the average permeability or porosity of the cigarettes and is coupled to a comparator which receives a reference signal from an adjustable potentiometer. The comparator output signal is applied to a servomotor which adjusts a resistor in series with the source supplying energy for generating the laser beam.

The system of the last mentioned patent alters web porosity as a function of resultant cigarette porosity and measures the latter through application of fluid under pressure. U.S. Pat. No. 3,258,117 discloses an alternate procedure for measuring cigarette porosity or permeability in which a fluid maintained at a constant flow is pulled through the cigarette and the pressure drop across the cigarette is measured and compared with the pressure drop across the standard through which the same flow is applied. In this case, the pneumatic system includes a vacuum pump coupled to a surge tank. The surge tank feeds a conduit having first and second needle valves for providing fine and course adjustement of the flow rate. A holder coupled to the conduit receives the cigarette to be tested and the pressure drop across the cigarette at the constant flow rate is automatically measured by a manometer. A valve in the conduit permits coupling the flow to a standard whose pressure drop is also read. Deviations of the pressure drop across the cigarette from the pressure drop across the standard indicate deviations in porosity or permeability from the preselected porosity of the standard.

It is a broad object of the present invention to provide an improved apparatus for measuring the porosity of a moving web of sheet material.

It is a further object of the present invention to provide a perforating system for perforating a moving web of cigarette paper including improved apparatus for measuring and controlling the porosity of the moving web.

SUMMARY OF THE INVENTION

In accordance with the principles of the present invention, the above and other objectives are realized in an apparatus comprising a sensor having a wall situated in adjacent relationship to the moving web of sheet material. The wall is provided with spaced apertures for obtaining an effective seal between the solid wall areas and the moving web during flow passing through the web and apertures and into a chamber of the sensor communicating with the apertures. Negative pressure is applied to the chamber through lines coupled to a common vacuum source and into which are inserted valves for maintaining the flow rate through the system at a substantially constant value. The seal between the web and wall permits air flow into the chamber primarily through the web and wall apertures, and the pressure drop across the wall is thereby found to be an accurate measure of web porosity.

When used in conjunction with a perforating system, pressure sensing means responsive to the pressure drop across the wall provides an output signal when the pressure drop lies outside a desired range of predetermined or preset values. Control means responsive to this output signal causes variation of the perforations being made in the web so as to bring the measured pressure drop within the desired range. Web porosity is thereby brought within a corresponding range of desired web porosities.

In a further aspect of the present invention, the sensor is arranged relative to the web such that the web passes from the fore and aft edges of the wall at an angle relative to the plane of the wall. This further enhances sealing between the wall and web. In preferred form, the fore and aft angles are within a range of 1 to 9 degrees.

BRIEF DESCRIPTION OF THE DRAWINGS

The above and other features and aspects of the present invention will become more apparent upon reading the following detailed description in conjunction with the accompanying drawings, in which.

DETAILED DESCRIPTION

Figure 1:
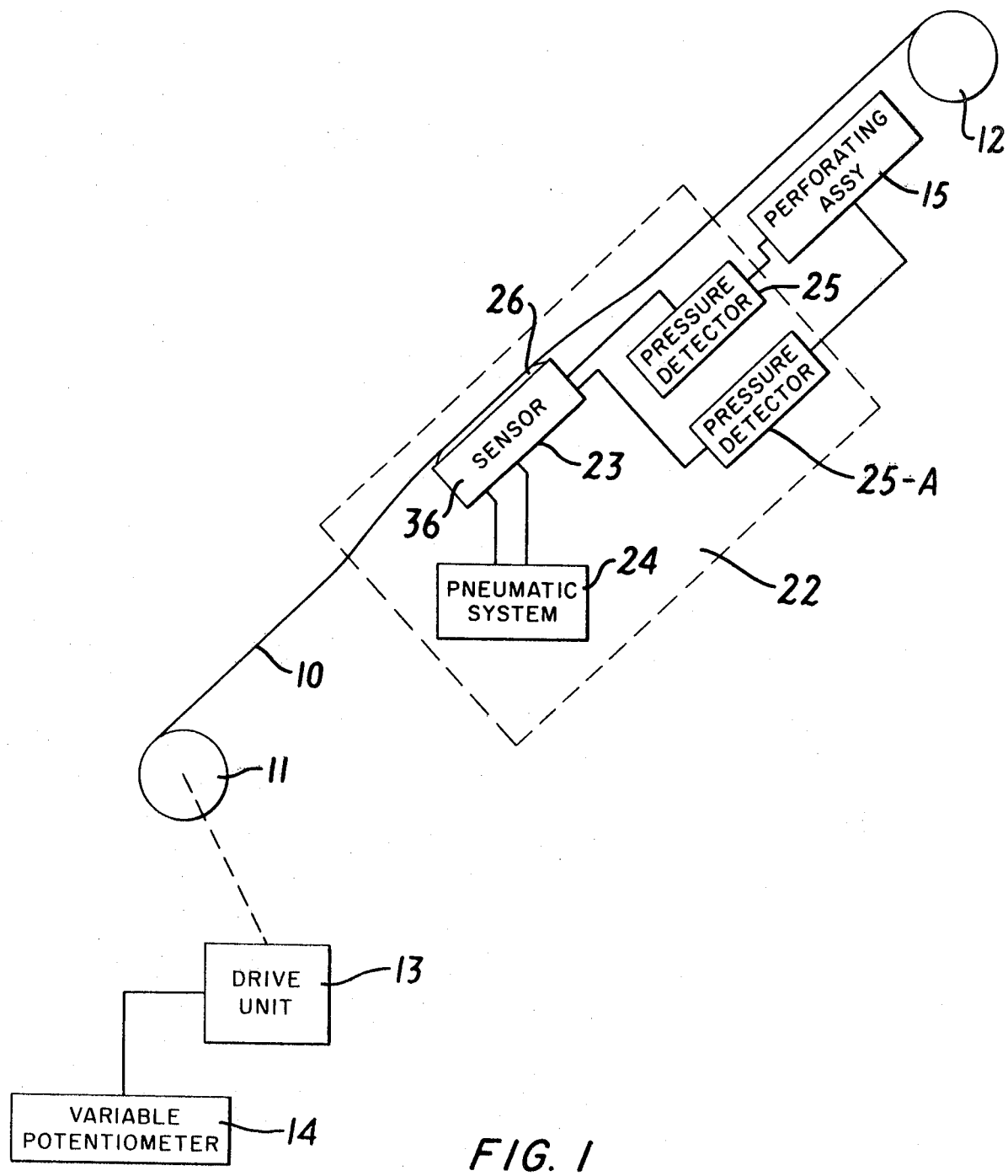
FIG. 1 shows partially in schematic and partially in block diagram a perforating system comprising a porosity measuring apparatus in accordance with the principles of the present invention.

In FIG. 1, a web 10 of sheet material is collected by a take-up drum 11 following transport from a payout drum 12. Takeup drum 11 is rotated by a drive unit 13 with a drum speed being established by a variable potentiometer 14 or like settable device.

Figure 2:
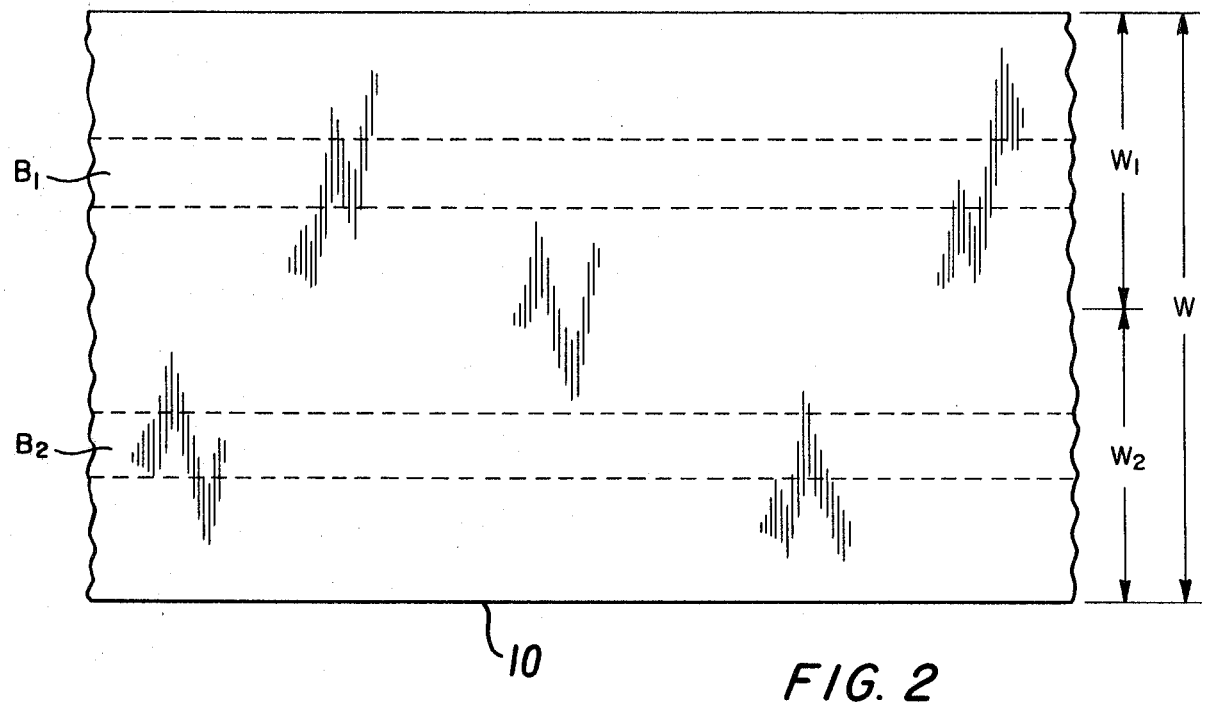
FIG. 2 illustrates a section of the web of FIG. 1 subsequent to perforation.

In the present illustrative example, the web 10 comprises tipping paper for covering or encasing the filter tips of cigarettes. As shown in FIG. 2, the web 10 is of double filter tip width W. The web is to be applied to the filter section of cigarette rods of double cigarette length, these rods then being subsequently severed centrally of the filter section to produce individual cigarettes. The half-widths $W_1$ and $W_2$ of the web thus each serve as a source of tipping paper for individual cigarettes.

Situated along the path of the web 10 is a perforating assembly 15 for providing perforations in each half-width $W_1$ and $W_2$ of the web to obtain a predetermined porosity. The latter is determined by the desired dilution characteristics of the individual cigarettes to be produced. In the present illustrative case, the perforating assembly provides corresponding bands $B_1$ and $B_2$ of perforations in the web halves $W_1$ and $W_2$. These perforation bands are desired to result in porosities of equal value $P_o$ in their respective web halves.

The perforations of the bands $B_1$ and $B_2$ may be of various ranges of sizes depending upon the particular cigarette application. Thus, for example, the perforations may have sizes in the millimeter range for a given application and sizes in the micron range for another application. Similarly, the distribution of the perforations can take on various characteristics. One example, is an ordered pattern of rows of perforations for the respective bands. The bands themselves may also vary in width for different applications.

Figure 6:
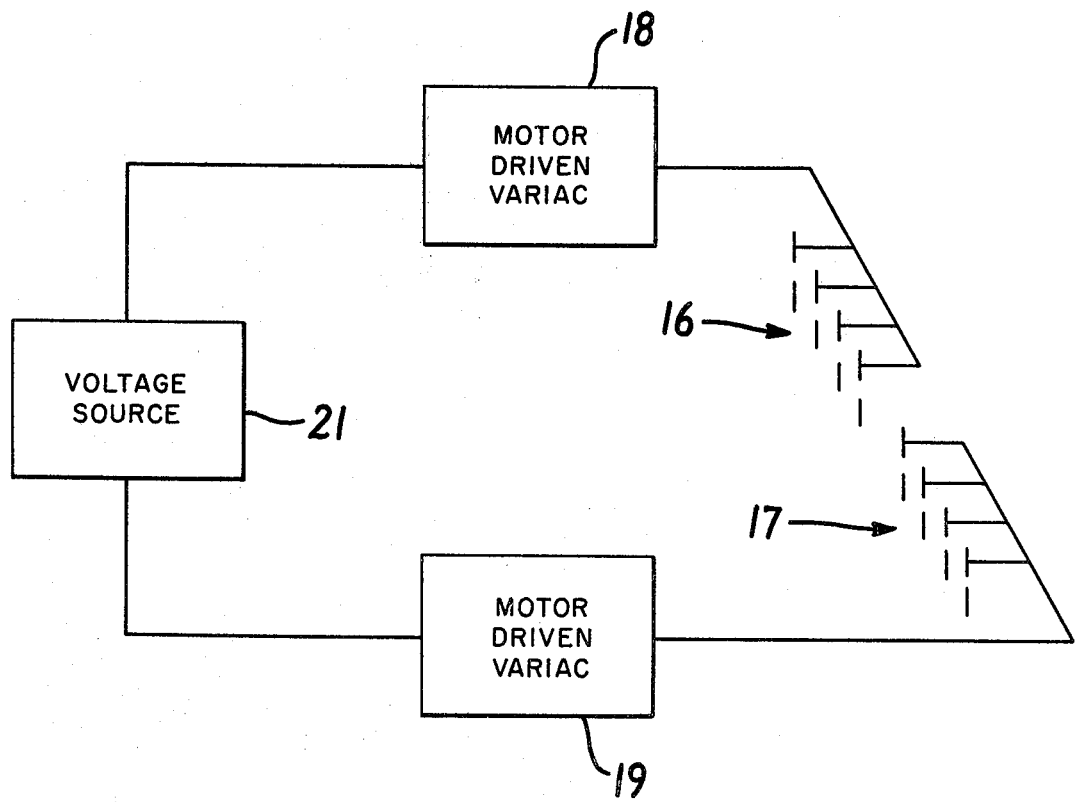
FIG. 6 illustrates also in schematic fashion the perforating assembly of the perforating system of FIG. 1.

The perforating assembly 15 can be of conventional laser or electric spark type. As illustrated in FIG. 6, the assembly is of electric spark type and comprises adjacent banks of opposing electrodes 16 and 17 for making the respective perforation bands $B_1$ and $B_2$. Energy is supplied to these electrode banks through motor driven variacs 18 and 19 coupled to a common voltage source 21. The variacs 18 and 19 permit independent variation of the energy being supplied to their respective electrode banks and, thus, independent control over the perforations of the bands $B_1$ and $B_2$.

As discussed hereinabove, the dilution characteristics of cigarettes produced with the web halves $W_1$ and $W_2$ are desired to be substantially invariant. This necessitates maintaining the porosity of the web halves within a predetermined or preset range or band of porosities centered about the porosity value $P_o$. In order to ensure this result, a porosity measuring apparatus and control assembly 22 is provided downstream of the perforating assembly 15. The assembly 22 monitors web porosity and generates signals for varying web porosity when web porosity is outside the desired range. Assembly 22 comprises a sensor or head 23, a pneumatic system 24 and pressure detectors 25 and 25A.

Figure 3B:
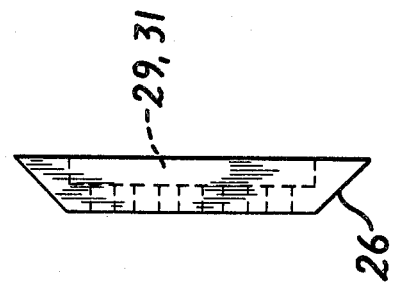
FIGS. 3A and 3B illustrate front and side views of the outer wall of the sensor of the porosity measuring apparatus of FIG. 1.
Figure 3A:
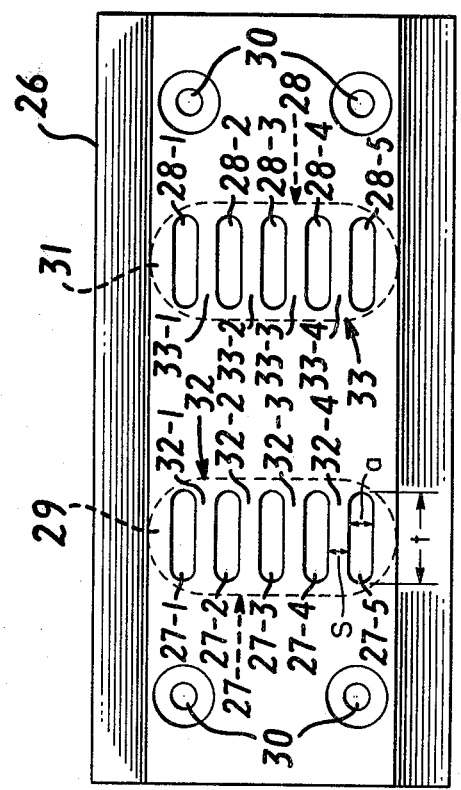

Sensor 23 is situated adjacent moving web 10, which is under tension, and is designed to effect a sealing relationship with the web without disturbing web velocity when a vacuum or negative pressure is created within the sensor. More specifically, the sensor 23 is provided with an outer wall 26 situated adjacent the web 10 and having apertures of spacing and dimension sufficient to produce an air seal between the solid wall portions and the web, while permitting the web to slide thereover so as not to disturb web velocity. FIGS. 3A and 3B show the outer wall 26 as a flat plate having bevelled lateral edges and first and second similar arrays 27 and 28 of spaced apertures 27-1 through 27-5 and 28-1 through 28-5. These apertures pass through the wall and open into elongate depressed areas 29 and 31 in the back surface of the wall. The spaces between the apertures of the two arrays define respective sets 32 and 33 of solid areas or lands 32-1 through 32-4 and 33-1 through 33-4.

Each aperture of the two arrays has transverse extent t and lateral extent a and adjacent apertures are spaced by the land width s, thereby providing a total lateral extent of $[(s+a)n-s]$ for each array, where n is the number of apertures. In the present illustrative case, the apertures of each array are five in number and each aperture is of the same dimension.

Figure 4:
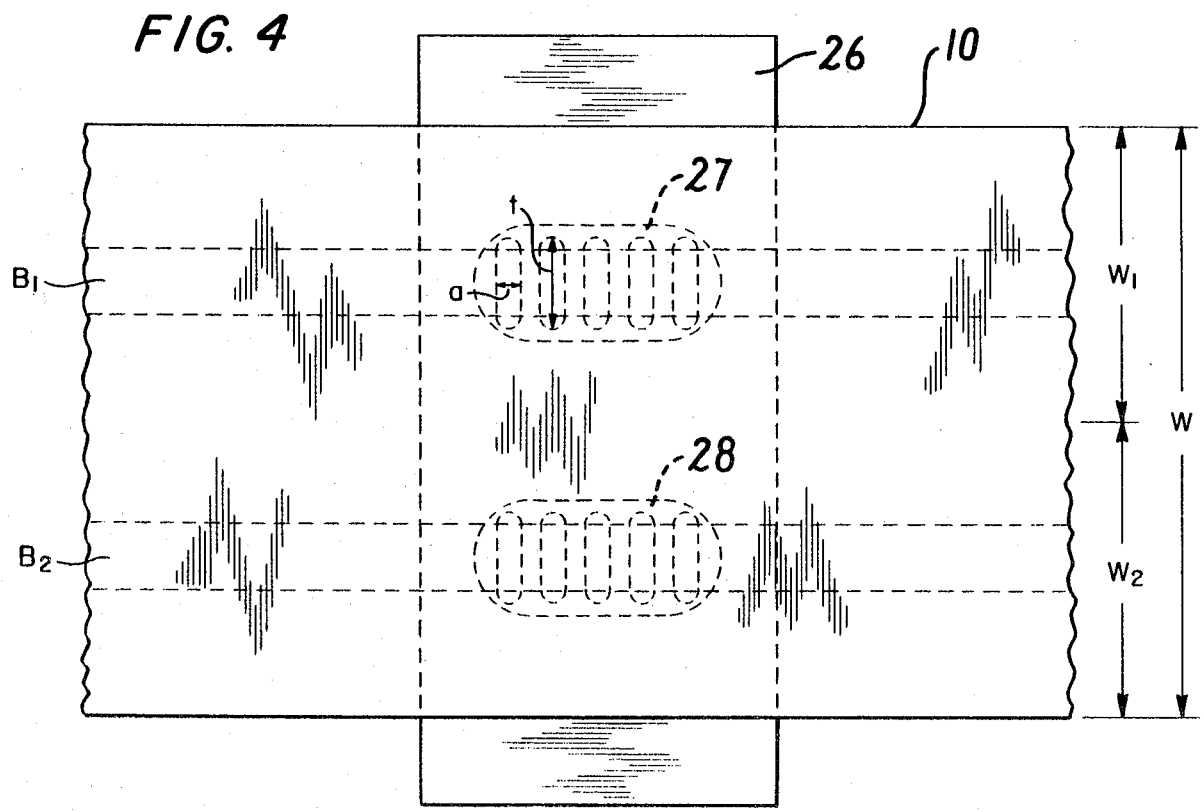
FIG. 4 illustrates the web and sensor outer wall in overlying relationship.

As shown in FIG. 4, the two aperture arrays 27 and 28 of the wall 26 align with the respective web halves $W_1$ and $W_2$ of the web 10. Array 27 thus permits monitoring of the porosity of the web half $W_1$ and array 28 monitoring of the porosity of the web half $W_2$. As can be further seen from FIG. 4, the aperture arrays 27 and 28 are aligned so that the transverse extents t of the apertures of each array cross the perforation band of the web half corresponding to that array. As shown, the transverse extent t of each aperture parallels the width of the web 10 and the lateral extent a the length of the web. As is also shown, the transverse extent t of each aperture is greater than the transverse extent of the corresponding perforation band.

With the aperture arrays 27 and 28 in the wall 26, an improved air seal occurs between the moving web and the solid wall areas or portions, upon application of a vacuum to the interior of the sensing member. This improved seal occurs at the lands 32-1 through 32-4 and 33-1 through 33-4 and is especially pronounced at the solid areas somewhat removed from the aperture edges. With this construction of the outer wall 26, air is thus forced to flow through the web, rather than around it, and into the apertures. Reliable sensing of the porosity of the web halves via the aperture arrays is therefore possible. This is in contrast to the use of a single aperture of equal open area in place of each of the arrays. In such case, effective sealing is not found to occur and the unsealed web and wall areas lead to unreliable porosity values.

Figure 5:
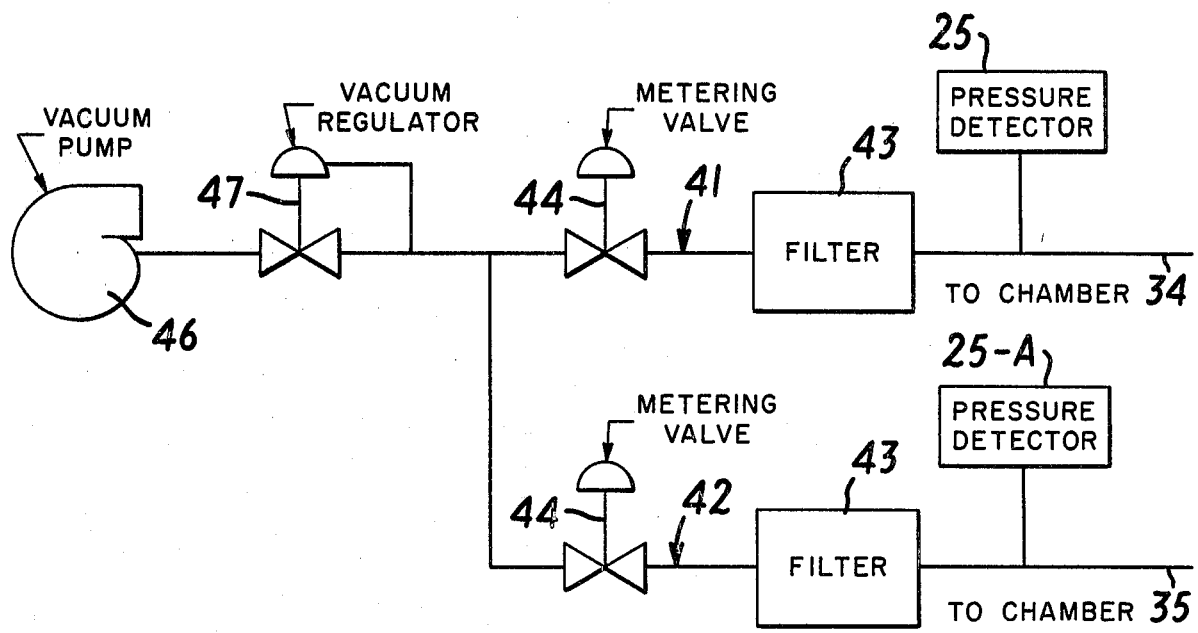
FIG. 5 shows in schematic fashion the pneumatic system of the porosity measuring apparatus of FIG. 1.

Communicating with each of the aperture arrays 27 and 28 in the wall 26 are separate chambers 34 and 35 of a support body 36 (FIGS. 7A through 7C) of the sensor 23. Air flow through the separate chambers and, hence, the arrays 27 and 28 and the corresponding web halves $W_1$ and $W_2$, is brought about by the pneumatic system 24. The system 24 is shown in FIG. 5 and comprises two similar air flow channels 41 and 42 which communicate with a vacuum pump 46 through a vacuum regulator 47. The flow channels 41 and 42 each include a metering valve 44 and a filter 43. The vacuum regulator 46 and metering valves 44 are set in conventional manner to establish air flows of constant similar flow velocities in the channels 41 and 42. Moreover, the flow channels between their respective filters and their respective chambers are of sufficiently low flow resistance that no appreciable pressure drop is experienced therebetween.

Air at such constant flow velocity, is thus drawn through the chambers 34 and 35, the aperture arrays 27 and 28 and the web halves $W_1$ and $W_2$. Due to the above-discussed air seal established between the web and outer wall 26, the respective air flows through the chambers 34 and 35 undergo pressure drops relative to the air pressure external to the web 10 which are accurate measures of the porosities of the web halves $W_1$ and $W_2$. These pressure drops when suitably detected can thus be used to vary operation of the perforating assembly 15 to ensure porosity values within the desired porosity range.

More particularly, pressure drop detection and comparison with pressure drops corresponding to the desired band of porosities is carried out by the respective pressure detectors 25 and 25A. The latter detectors communicate with the respective air channels 41 and 42 adjacent the connection of same with the chambers 34 and 35. Detectors 25 and 25A, are further electrically coupled to variacs 18 and 19 of the perforating assembly 15. When the pressure drop detected by a respective detector indicates an out of range pressure drop and, hence, an out of range porosity for its respective web half, the detector provides a suitable signal to its respective variac. The latter, in turn, changes value to alter electrode excitation in a manner to vary porosity toward the desired range. In typical control system fashion, the detectors 25 and 25A thus act to alter porosity of the web havles to ensure porosity values within the desired range.

Figure 7A:
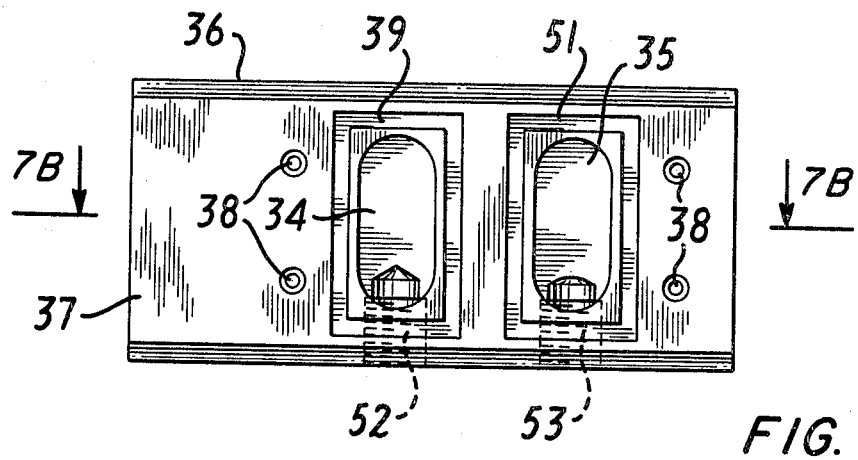
FIG. 7A illustrates a front view of the support body of the sensor of FIG. 1.
Figure 7B:
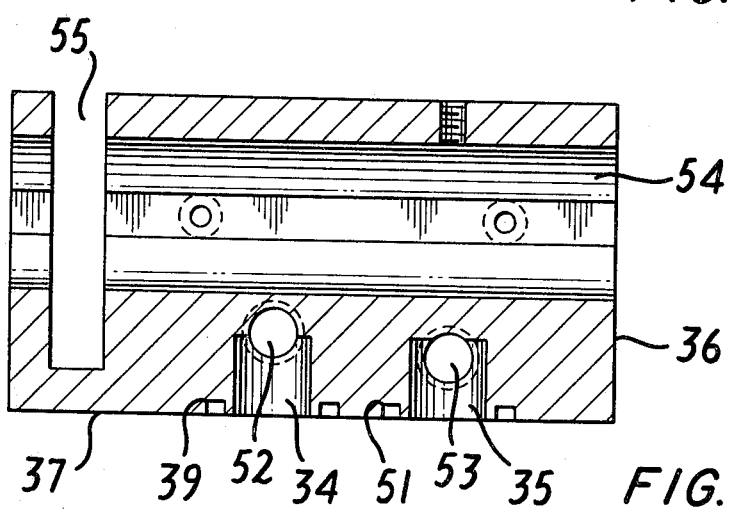
FIG. 7B shows a cross section of the support body of FIG. 7A taken along the line 7B—7B of FIG. 7A.
Figure 7C:
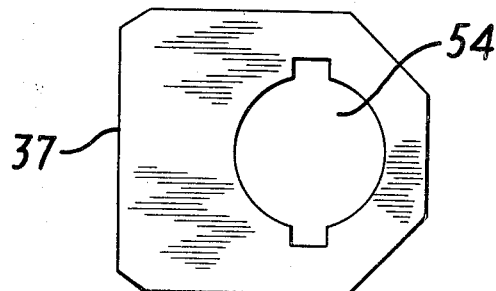
FIG. 7C shows a side view of the support body of FIG. 7A.

As above-noted, the support body 36 of the sensor 23 is provided with chambers 34 and 35 which communicate with the respective aperture arrays 27 and 28 of the outer wall 26. The chambers 34 and 35 open out of a front surface 37 of the body 36 as shown in FIGS. 7A and 7B. This surface seats the rear surface of the outer wall 26 and is provided with threaded holes 38. Corresponding holes 30 in the wall 26 are provided for receiving screws which pass into the threaded holes 38, thereby securing the wall to the support body.

Grooves 39 and 51 are provided in the surface 37 bordering the peripheries of the chambers 34 and 35 for receiving O-rings. These rings provide a seal between the rear surface of the wall 26 and the surface portions of the surface 37 bordering the chambers 34 and 35. Air flowing through the wall apertures is thus confined to the chambers and leakage at the wall-body interface is prevented.

Bores 52 and 53 communicate with the lower regions of the respective chambers 34 and 35. These bores further communicate with the flow channels 41 and 42 and enable vacuum to be established within their respective chambers.

Below the chambers 34 and 35 a central axial channel 54 extends through the support body. This bore is provided for receiving a support shaft (not shown) having a threaded end which is engaged by a knurled knob (not shown) which is to be received in a radial slot 55 of the body. The support shaft and knob permit relative axial displacement of the support body, thereby permitting same to be adjustably situated along the web width.

As can be appreciated, the components utilized for the assemblies of the present invention will depend upon the particular application. Typically, the pressure detectors 25 and 25A can be Series 3000 photohelic pressure switch gauges manufactured by Dwyer Instruments Incorporated. Similarly, the metering valves, filters, vacuum regulator and vacuum pump of the pneumatic system can all be standard off the shelf components. Thus, the vacuum regulator 47 might be a Model No. 16113 Fairchild regulator, while the metering valve 44 might be B-4MA valves manufactured by Nupro. Balston type 92 filters might be used for the filters 43. Similarly, standard components can be utilized for the variable potentiometer of the web transport and the motor driven variacs of the perforating assembly.

In actual practice, the number, dimensions and spacing of the apertures of the arrays 27 and 28 to achieve the above-described improved air sealing relationship for a given area or expanse of the web 10 to be monitored, will depend upon a variety of parameters, including, for example, the web characteristics, the web tension, the constant air flow rate, and the web perforation sizes. These parameters will of course themselves depend upon the particular application and for each application emperical determination of the array characteristics can be made. One example of typical array parameters for use in porosity measurement of bands of millimeter width having micron size perforations is as follows:

number of apertures per array: 5
aperture transverse dimension t: $\frac{3}{8}$ inch
aperture lateral dimension a: $\frac{1}{8}$ inch
aperture spacing s: $\frac{1}{8}$ inch
Air flow when using these parameters can be maintained, for example, at a substantially constant rate of 700 cc/min. Web tension, typically might be 10 lbs.

In the present illustrative example, the perforating assembly was illustrated as comprising separate perforating sections for producing each of the perforation bands $B_1$ and $B_2$. In some perforating units such as, for example, some laser perforating units a single section or source provides both perforation bands. With this type of perforating unit, control of web porosity might be carried out by utilizing one of the signals of the detectors 25 and 25A to control web transport speed rather than perforating assembly characteristics. In such cases the detector signal would be applied to the transport variable potentiometer 14. Furthermore, in this circumstance, the second detector might be used merely as a monitor to observe whether the porosity of its respective band is in correspondence with that of the band whose detector is providing web speed control. As is also apparent, the present invention could be utilized in conjunction with tipping paper of single cigarette width, with cigarette paper or with any type of sheet material, in which case only one array of outer wall apertures would be required as well as only one pressure detector and air flow channel.

Figure 8:
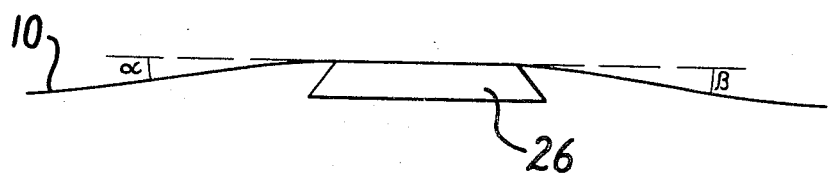
FIG. 8 shows an enlarged view of the web as it passes over the outer wall of the sensor.

In a further aspect of the present invention, the sensor 23 is situated relative to the moving web 10 such that the plane of the web at the ends of the outer wall 26 is at a slight angle with respect to the plane of the wall. This is illustrated more clearly in the enlarged view of FIG. 8. As shown, the web 10 fore and aft of the edges of the flat lateral expanse of the wall 26 is at slight angles $\alpha$ and $\beta$ relative to the plane of the wall. Typically, the angles $\alpha$ and $\beta$ should be greater than approximately 1 degree and a preferred range would be between 1 and 9 degrees. Additionally, it is further preferred that the angles be approximately equal. With this arrangement of the sensor, the air-seal effect described hereinabove is further improved with a corresponding improvement in porosity control.

In all cases, it is understood that the above-described arrangements are merely illustrative of the many possible specific embodiments which represent applications of the present invention. Numerous and varied other arrangements can readily be devised in accordance with the principles of the present invention without departing from the spirit and scope of the invention. Thus, for example, instead of utilizing a vacuum to cause air flow through the chambers 34 and 35, aperture arrays 27 and 28 and web 10, a positive source of air pressure could have been situated exterior to the web and directed from the web exterior through the web, the apertures and into the chambers.

What is claimed is:

1. Apparatus for use with a moving web of sheet material comprising:
    means for transporting said web of sheet material along a predefined path;
    a sensor for measuring the porosity of said web, said sensor having a chamber and comprising a wall disposed adjacent said moving web, said wall having first and second ends transverse to said path and over which said web initiates and terminates movement past said sensor, said wall further having first and second solid end sections extending from said first and second ends to the interior of said wall, and interior of said solid end sections about five apertures of lateral expanse in the direction of said path of about ⅛ and spaced from one another by lands of expanse in the direction of said path of about ⅛ inch, said apertures communicating with said chamber;
    and means for subjecting said chamber to a pressure differential, whereby a seal is obtained between said moving web and said wall during flow through said web and said apertures and into said chamber.

2. Apparatus in accordance with claim 1 further comprising:
    means for detecting the pressure drop across said wall.

3. Apparatus in accordance with claim 2 wherein:
    said detecting means communicates with said chamber.

4. Apparatus in accordance with claim 3 wherein:
    said means for subjecting creates a vacuum in said chamber.

5. Apparatus in accordance with claim 4 wherein:
    said means for subjecting includes valve means for maintaining the air flow through said chamber at a substantially constant valve.

6. Apparatus in accordance with claim 1 wherein the porosity of said sheet material is to be measured over a predetermined area of said sheet material and said apertures have a total area substantially equal to said predetermined area.

7. Apparatus in accordance with claim 1 wherein:
    said apertures are arranged in a row.

8. Apparatus in accordance with claim 7 wherein:
    said apertures are five in number.

9. Apparatus in accordance with claim 1 wherein:
    said wall comprises a flat plate; and said sensor further comprises a support body for said plate, said support body including said chamber.

10. Apparatus in accordance with claim 1 wherein:
    said sensor is positioned such that said web passes in adjacent facing relationship to said wall and at said first and second ends of said wall is at an angle relative to the plane of said wall.

11. Apparatus in accordance with claim 10 wherein:
    p1 said angle is equal to or greater than one degree at both said wall ends.

12. Apparatus in accordance with claim 11 wherein:
    said angle is within the range of one to nine degrees at both said wall ends.

13. Apparatus in accordance with claim 10 wherein:
    said angle at both said wall ends is approximately the same.

14. Apparatus in accordance with claim 10 wherein:
    said wall is flat.

15. Apparatus in accordance with claim 1 further comprising:
    a perforating assembly for perforating said web of sheet material; and
    means for detecting the pressure drop across said wall.

16. Apparatus in accordance with claim 15 wherein:
    said detecting means includes means for generating a signal when said pressure drop is out of a predetermined range of pressure drops, said signal being indicative of the need to alter the perforations being made in said web.

17. Apparatus in accordance with claim 16 wherein:
    said perforating assembly includes means responsive to said signal for changing operation of said perforating assembly to vary the perforations being made in said web.

18. Apparatus in accordance with claim 16 further comprising:
    means for transporting said web.

19. Apparatus in accordance with claim 16 wherein:
    said transport means includes means responsive to said signal for changing the speed of transport of said web to alter the perforations being made in said web.

20. Apparatus in accordance with claim 17 or 19 wherein:
said perforating assembly is an electric spark perforating assembly.

21. Apparatus in accordance with claim 19 wherein:
said perforating assembly is a laser perforating assembly.

22. Apparatus in accordance with claim 15 wherein: said subjecting means includes:
vacuum means; and a flow channel communicating with said vacuum means and said chamber;
and said detecting means communicates with said chamber.

23. Apparatus in accordance with claim 16 wherein:
said sheet material is cigarette paper.

24. Apparatus in accordance with claim 23 wherein:
said cigarette paper is tipping paper.

* * * * *